(12) United States Patent
Kusumoto

(10) Patent No.: US 7,296,466 B2
(45) Date of Patent: Nov. 20, 2007

(54) UNDERWATER WEIGHING CONTAINER AND APPARATUS FOR MEASURING SPECIFIC GRAVITY

(75) Inventor: Tetsuro Kusumoto, Uji (JP)

(73) Assignee: Shimadzu Corporation, Kyoto (JP)

( * ) Notice: Subject to any disclaimer, the term of this patent is extended or adjusted under 35 U.S.C. 154(b) by 97 days.

(21) Appl. No.: 11/047,889

(22) Filed: Jan. 31, 2005

(65) Prior Publication Data

US 2005/0210975 A1 Sep. 29, 2005

(30) Foreign Application Priority Data

Mar. 25, 2004 (JP) ............................. 2004-088926

(51) Int. Cl.
*G01N 9/10* (2006.01)
(52) U.S. Cl. ........................................... 73/437
(58) Field of Classification Search .................. 73/433, 73/437; 177/207; 209/259
See application file for complete search history.

(56) References Cited

U.S. PATENT DOCUMENTS

| | | | | |
|---|---|---|---|---|
| 1,760,658 A | * | 5/1930 | Pampe | ...................... 73/32 R |
| 2,045,813 A | * | 6/1936 | Waterbury | .................... 209/239 |
| 3,747,416 A | * | 7/1973 | Wommack | .................... 73/437 |
| 3,777,892 A | * | 12/1973 | Thijssen et al. | ............ 210/178 |
| 4,243,856 A | * | 1/1981 | Gratzmuller | ............... 200/81.5 |
| 4,372,405 A | * | 2/1983 | Stuart | ....................... 177/25.14 |
| 4,770,041 A | * | 9/1988 | Bearce | .......................... 73/437 |
| 6,098,454 A | * | 8/2000 | Ghorashi et al. | .............. 73/160 |
| 6,101,874 A | * | 8/2000 | Shemoney | .................... 73/437 |
| 6,561,025 B2 | * | 5/2003 | Ueno | .......................... 73/437 |
| 7,194,951 B1 | * | 3/2007 | Porter | ......................... 100/116 |

FOREIGN PATENT DOCUMENTS

| | | |
|---|---|---|
| CN | 1370986 | 9/2002 |
| JP | 11-230885 | 8/1999 |
| JP | 2002-243615 | 8/2002 |
| JP | 2003-307482 | 10/2003 |

\* cited by examiner

*Primary Examiner*—Hezron Williams
*Assistant Examiner*—John Fitzgerald
(74) *Attorney, Agent, or Firm*—J.C. Patents

(57) ABSTRACT

An underwater weighing container for measuring specific gravity, requiring relatively a small amount of reference liquids for measurement and offering wide space for mounting specimens to be measured are provided. The underwater weighing container includes a tubular body and a circular bottom plate. The tubular body has openings on both ends. One end has an introvert circular rim formed thereon and the other end has a plurality of stoppers attached to the internal surface thereof. The circular bottom plate has a mesh or a porous structure and is inserted between the circular rim and the stoppers. The underwater weighing container is immersed in a reference liquid, and a solid specimen is placed on or inserted underneath the bottom plate. The underwater weighing container is hung by means of a hanging member 13 to measure the weight of the solid specimen and determine the specific gravity.

9 Claims, 5 Drawing Sheets

UNDERWATER WEIGHING CONTAINER AND APPARATUS FOR MEASURING SPECIFIC GRAVITY

CROSS-REFERENCE TO RELATED APPLICATION

This application claims the priority benefit of Japan application serial no. JP2004-088926, filed on Mar. 25, 2004.

BACKGROUND OF THE INVENTION

1. Field of the Invention

The present invention relates to an underwater weighing container and an underwater weighing container unit for receiving a weight of a solid specimen immersed in a reference liquid and a buoyant force exerted thereon. The present invention also relates to an apparatus for measuring a specific gravity of the solid specimen.

2. Description of the Related Art

Generally, the commonly employed method for determining a specific gravity of a solid specimen without knowledge of its volume is to weigh the solid specimen in air, measure a weight of the solid specimen immersed in a reference liquid or a buoyant force exerted thereon, and use the obtained values for calculating the relevant specific gravity based on the following equation (1):

Specific Gravity=Weight in Air/(Weight in Air−
  Weight in Liquid)=Weight in Air/Buoyant Force   Equation (1)

As will be exemplified hereinafter, methods of weighing a solid specimen both in air and in a reference liquid, or measuring a weight of the solid specimen in air and a buoyant force produced by the solid specimen, for calculation of the relevant specific gravity have been applied to a number of conventional apparatus for measuring specific gravity. One such example is a specific gravity measuring apparatus 5A in FIG. 8, wherein a solid specimen 2 is first hung and suspended in air and then placed inside a liquid bath 3 to measure its weight by means of an electronic weighing scale 7, for determining the specific gravity. As shown in FIG. 9, another conventional specific gravity measuring apparatus 5B has an underwater weighing container 1A arranged on an electronic weighing scale 7, allowing the underwater weighing container 1A to mount a solid specimen 2 thereon in a liquid bath 3B. With this configuration, after the underwater weighing container 1A holding the solid specimen 2 is subjected to measurement, the corresponding tare weight is subtracted from the obtained weight to determine specific gravity of the solid specimen 2. The patent literatures pertaining to these apparatuses for measuring specific gravity are Unexamined Japanese Patent Application Publication Nos. H11-230885 and 2002-243615.

The aforementioned configurations are employed in the conventional specific gravity measuring apparatus and the underwater weighing containers. However, the method of hanging and suspending the solid specimen 2 as shown in FIG. 8 is troublesome, due to the need to replace and suspend the solid specimen 2 having different shapes. In the method of providing the underwater weighing container 1A for measuring the weight of the solid specimen 2, as shown in FIG. 9, the solid specimen 2, if its specific gravity is lower than that of a reference liquid, will be floating. As representative measures to prevent the solid specimen 2 from floating, a sinker frame 8 as shown in FIG. 9, or a lid (not illustrated) may be placed in a reference liquid L. If any such measure is to be implemented, users will be required to insert and remove the sinker frame 8 or to open and close the lid, whenever conducting weight measurement. This method, as illustrated in FIG. 8, is inconvenient for users. Depending on whether the solid specimen 2 sinks or floats in the reference liquid L, users will be required to employ a different configuration of the underwater weighing container 1A. This can increase users' work load for maintenance and management of the apparatus for measuring specific gravity. The amount of the reference liquid L used for the measurement process also increases.

SUMMARY OF THE INVENTION

In consideration of the situation presented heretofore, the present invention is provided. An object of the present invention is to provide an underwater weighing container and a specific gravity measuring apparatus using the same, which can be applied to a solid specimen that may be heavier or lighter than the reference liquid. In addition, the underwater weighing container and the specific gravity measuring apparatus are compact and require relatively a small amount of reference liquid used for the weight measurement.

In order to accomplish the aforementioned object, the present invention provides an underwater weighing container, equipped with a bottom plate movable both upwardly and downwardly within a given range. Furthermore, the bottom plate is designed to hold a solid specimen on the upper surface thereof and carry its weight thereon if the specific gravity of the solid specimen is higher than that of a reference liquid, or to place the solid specimen underneath the bottom plate for a buoyant force of the specimen to be exerted against the bottom plate if the specific gravity of the solid specimen is lower than that of the liquid.

In one embodiment of the present invention, the present invention further provides an underwater weighing container unit, comprises an underwater weighing container being arranged at a lower position, a bottom plate capable of moving both upward and downward in a given range, an aerial weighing container arranged at an upper position to carry the weight of a solid specimen in air, and coupling rods to couple with the underwater weighing container and the aerial weighing container.

Furthermore, apparatus for measuring specific gravity of the present invention comprises the underwater weighing container unit of the present invention, a frame supporting the underwater weighing container unit, and a weight measuring unit, the frame being placed on the weight measuring unit to determine the specific gravity of a solid specimen.

An underwater weighing container, an underwater weighing container unit and apparatus for measuring specific gravity according to the present invention have the aforementioned configurations, wherein a bottom plate of the underwater weighing container are movable so as to place and hold a solid specimen inside whenever the solid specimen is subjected to measurement in a reference liquid.

For this reason, they occupy a relatively small space and enable users to effectively reduce the amount of reference liquid used for the measurement process.

In an underwater weighing container, an underwater weighing container unit and apparatus for measuring specific gravity according to the present invention, the underwater weighing container is equipped with a movable bottom plate. If a solid specimen is heavier than a reference liquid, the solid specimen is placed on the bottom plate and moved downward with the associated bottom plate by their gravity. If the solid specimen is lighter than the reference liquid, the solid specimen is inserted underneath the bottom plate and moved upward with the associated bottom plate by the specimen's buoyant force. Consequently the solid specimen remains inside the underwater weighing container in any case. Thus, it is possible to reduce the size of underwater weighing container, underwater weighing container unit, apparatus for measuring specific gravity, and a liquid bath used therein, and also to reduce the amount of reference liquids used for measurement.

BRIEF DESCRIPTION OF THE DRAWINGS

FIG. 1A shows a front elevation view of the underwater weighing container 1, and FIG. 1B shows a cross-sectional side elevation thereof.

FIG. 2A shows a condition where a solid specimen to be measured is heavier than a reference liquid, and FIG. 2B shows the other condition where the solid specimen is lighter than the reference liquid.

FIGS. 3A and 3B are a partial cross-sectional front elevation view and a plan view of the underwater weighing container unit 4, respectively.

FIG. 6(a) shows a condition where a solid specimen to be measured is heavier than a reference liquid, while FIG. 6(b) shows the other condition where the solid specimen is lighter than the reference liquid.

DESCRIPTION OF THE PREFERRED EMBODIMENTS

The present invention will be discussed hereinafter in detail in terms of the preferred configurations and functions of an underwater weighing container, an underwater weighing container unit and apparatus for measuring specific gravity according to the present invention with reference to the accompanying drawings. In the following description, numerous specific details are set forth in order to provide a thorough understanding of the present invention. It will be obvious, however, to those skilled in art that the present invention may be practiced without these specific details. In other instance, well-known configurations are not shown in detail in order to avoid unnecessary obscurity of the present invention.

Figure 1A:
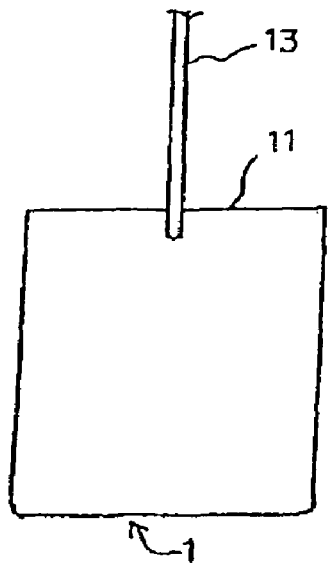
FIGS. 1A and 1B show a configuration of an underwater weighing container 1.
Figure 1B:
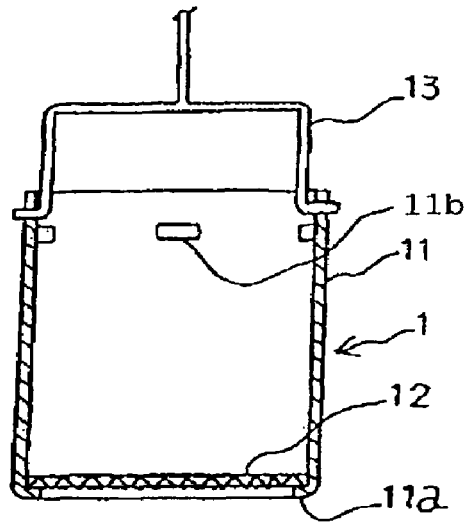

FIGS. 1A and 1B show a structure of an underwater weighing container 1 according to one embodiment of the present invention. FIG. 1A shows a front elevation view of the underwater weighing container 1, while FIG. 1B shows a cross-sectional side elevation view thereof.

The underwater weighing container 1 comprises a metallic tubular body 11 having openings on both ends, wherein one end of the openings has a circular rim 11a produced through such processes as bending and/or welding and the other end of the opening has four stoppers 11b on the internal surface, wherein the four stoppers are arranged with each fixed at 90 degrees from the central axis of the tubular body 11 . The underwater weighing container 1 further comprises a circular metallic bottom plate 12 having a mesh or a porous structure and being inserted between the circular rim 11a and the stoppers 11b; and a metallic hanging member 13 being attachable to the upper part of the tubular body 11 for hanging and suspending the tubular body 11. The bottom plate 12 is basically configured in contact with the circular rim 11a. When a buoyant force that is greater than the weight of the bottom plate 12 is exerted to the bottom plate 12 from underneath, the bottom plate 12 can move upward until it reaches where the stoppers 11b are installed.

Figure 2A:
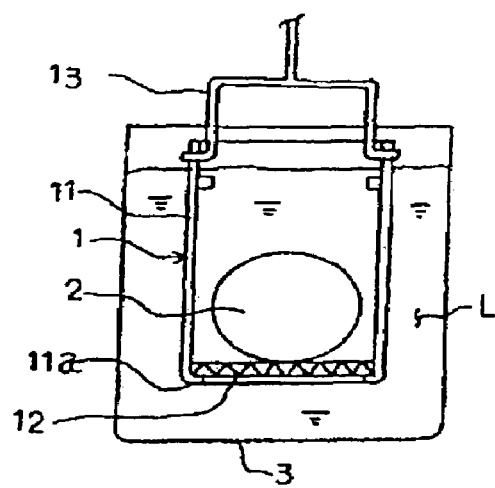
FIGS. 2A and 2B show cross-sectional front elevation views of the underwater weighing container 1 during use.
Figure 2B:
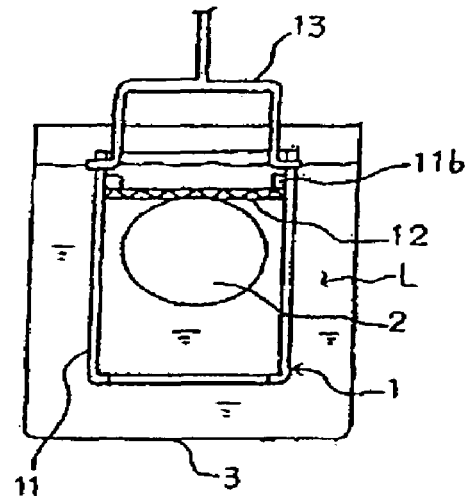

FIGS. 2A and 2B show cross-sectional front elevation views of the underwater weighing container 1 holding a solid specimen 2. FIG. 2A shows a condition that the specific gravity of the solid specimen 2 is larger than that of a reference liquid L, and FIG. 2B shows the other condition where the specific gravity of the solid specimen 2 is smaller than that of the reference liquid L. A method of measuring specific gravity of the solid specimen 2 by using the underwater weighing container 1 is described hereinafter with reference to FIGS. 2A and 2B.

First, while the underwater weighing container 1 is submerged in a liquid bath 3, a weighing apparatus (not shown in FIGS. 2A and 2B) such as a scale, together with a hanging member 13 is employed, to measure the weight (W0) of the underwater weighing container 1 per se. If the solid specimen 2 is heavier than the reference liquid L, the solid specimen 2 is placed on the bottom plate 12 as shown in FIG. 2A, and at which time the weight W1 of the underwater weighing container 1 with the solid specimen 2 is measured. If the weight of the solid specimen 2 measured in air is Wa, the specific gravity S of the solid specimen 2 can be calculated based on the following equation (2).

$$S=Wa/(Wa-(W1-W0)) \qquad \text{Equation (2)}$$

If the specific gravity of the solid specimen 2 is smaller than that of the reference liquid L, the underwater weighing container 1 is lifted to insert the solid specimen 2 underneath the bottom plate 12 as shown in FIG. 2B. Due to the buoyant force produced thereby, the solid specimen 2 is in contact with the bottom plate 12, and moves upward together with the bottom plate 12 until the solid specimen 2 remain stationary and stable. Under this condition, the weight (W2) of the underwater weighing container 1 is determined. Accordingly, the specific gravity S of the solid specimen 2 can be calculated based on the following equation (3).

$$S=Wa/(W0-W2) \qquad \text{Equation (3)}$$

Figure 3A:
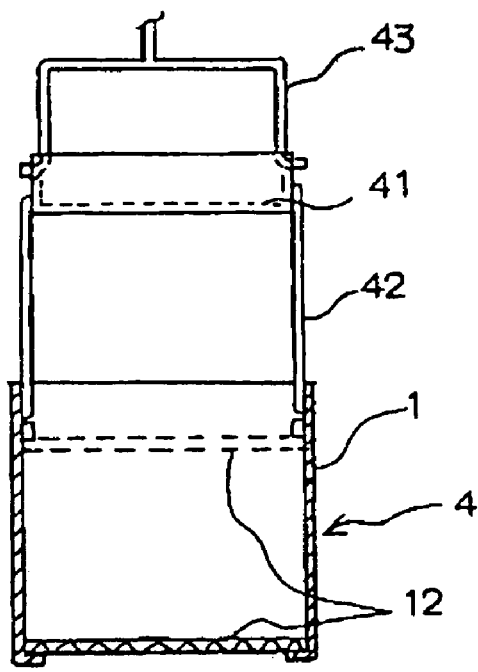
FIGS. 3A and 3B show a configuration of an underwater weighing container unit 4.
Figure 3B:
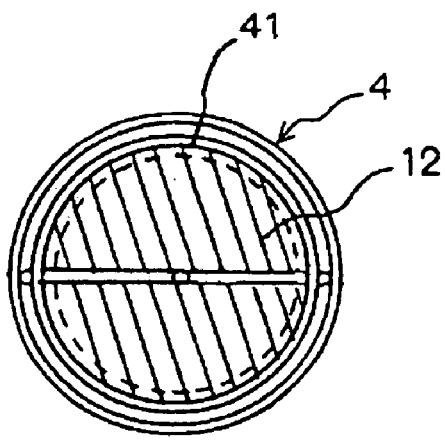

FIGS. 3A and 3B show a structure of an underwater weighing container unit 4 according to another embodiment of the present invention. FIG. 3A shows a partial cross-sectional front elevation view of the underwater weighing container unit 4, and FIG. 3B shows a plan view thereof. The underwater weighing container unit 4 comprises the underwater weighing container 1 arranged in a lower position; an aerial weighing container 41 being a circular container made either of metal or resin, arranged in an upper position; coupling rods 42 coupling with the underwater weighing container 1 and the aerial weighing container 41; and a hanging member 43 attached to the aerial weighing container 41. Based on this configuration, a solid specimen can be solid received in the aerial weighing container 41 to measure its weight in air, and the solid specimen can be placed on or underneath the bottom plate 12, so that the weight of the solid specimen immersed in a reference liquid or the buoyant force exerted thereon can be weighted.

Figure 4:
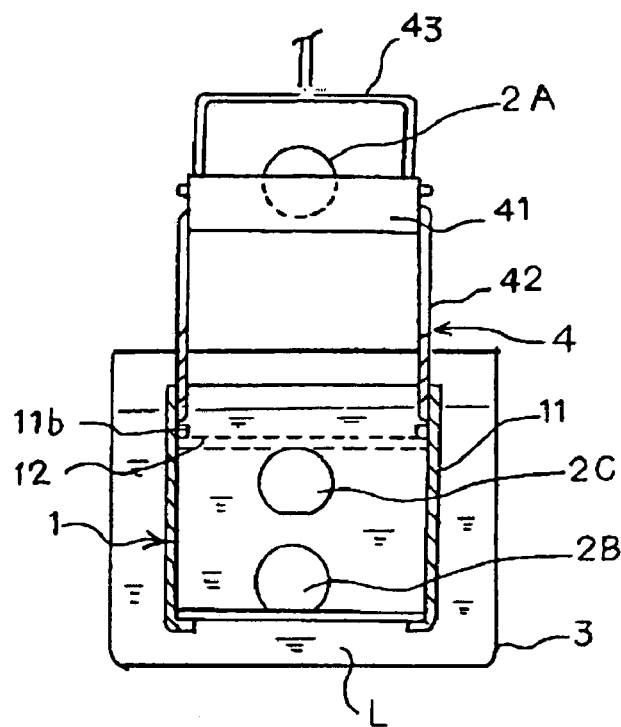
FIG. 4 shows a partial cross-sectional front elevation view of the underwater weighing container unit 4 during use.

FIG. 4 is a partially cross-sectional front elevation view of the underwater weighing container unit 4, wherein solid specimens 2A, 2B and 2C are received in the liquid bath 3. The disposition of the solid specimen 2A in FIG. 4 represents a position designated for measuring its weight in air. The disposition of the solid specimen 2B represents a position designated for measuring its weight in the reference liquid L, wherein the solid specimen 2B is placed on the bottom plate 12 and submerged in the reference liquid L if the specific gravity of the solid specimen 2B is larger than that of the reference liquid L. The disposition of the solid specimen 2C represents a position designated for measuring its buoyant force in the reference liquid L, wherein the solid specimen 2C is inserted underneath the bottom plate 12 and submerged in the reference liquid L if the specific gravity of the solid specimen 2C is smaller than that of the reference liquid L. A method of measuring the specific gravities of the solid specimens 2A, 2B and 2C respectively by means of the underwater weighing container unit 4 is described hereinafter with reference to FIG. 4.

First, while only the underwater weighing container unit 4 is dipped and immersed in the liquid bath 3, a weight measuring apparatus (not shown in FIG. 4) such as a scale, together with a hanging member 43, is employed to measure the weight W0 of the underwater weighing container unit 4 per se. The solid specimen 2A is arranged on the underwater weighing container unit 4, at which time the weight W1 of the underwater weighing container unit 4 is measured. If the solid specimen is heavier than the reference liquid L, the solid specimen is placed in the designated position as shown by the solid specimen 2B of FIG. 4, and under this condition, the weight W2 of the underwater weighing container unit 4 with the solid specimen 2B is measured. Hence, the specific gravity S of the solid specimen 2B can be calculated based on the following equation (4).

$$S=(W1-W0)/(W1-W2) \qquad \text{Equation (4)}$$

If the solid specimen is lighter than the reference liquid L, the underwater weighing container unit 4 is lifted to insert the solid specimen underneath the bottom plate 12, as indicated by the solid specimen 2C in FIG. 4. With the buoyant force produced thereby, the solid specimen 2C floats, makes contact with the bottom plate 12, moves upward together with the bottom plate 12 until reaching up to the locations of the stoppers 11b. The solid specimen 2C then remains stationary and stable. Under this condition, the weight W3 of the underwater weighing container unit 4 with the solid specimen 2C is measured. Therefore, the specific gravity S of the solid specimen 2C can be calculated based on the following equation (5).

$$S=(W1-W0)/(W0-W3) \qquad \text{Equation (5)}$$

Figure 5:
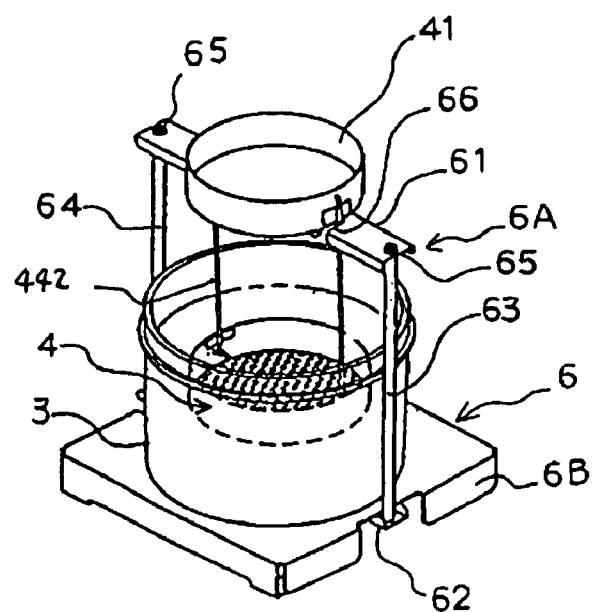
FIG. 5 shows a perspective view of a specimen mounting unit 6 associated with an example of the present invention.

FIG. 5 is a perspective view of a specimen mounting unit 6 used in specific gravity measuring apparatus 5 according to another embodiment of the present invention, which will be mentioned later. The specimen mounting unit 6 comprises the underwater weighing container unit 4; a frame 6A supporting the underwater weighing container unit 4; a liquid bath 3 containing a reference liquid to hold the underwater weighing container unit 4 completely submerged therein; a liquid bath mounting platform 6B to place the liquid bath 3 thereon while straddling a lower frame 62 of the frame 6A.

The frame 6A comprises an upper frame 61; the lower frame 62 mounted and installed on a weighing pan 71 of an electronic weighing scale 7 to be described later; coupling rods 63 and 64 and setscrews 65 connecting the upper frame 61 with the lower frame 62 at a certain height. V-shaped notched-portions 66 that are able to hold or remove the underwater weighing container unit 4 are arranged on the upper frame 61 based on a gap between the coupling rods 63 and 64. The underwater weighing container unit 4 is supported by the frame 6A, when the coupling rods 42 pass through the notched-portions 66. The underwater weighing container unit 4 can be removed from the frame 6A by lifting the aerial weighing container 41 and drawing the coupling rods 42 out of the notched-portions 66.

Figure 6A:
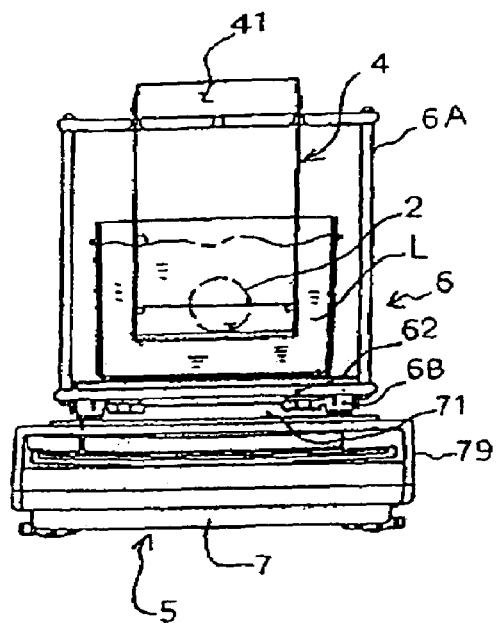
FIG. 6A and 6B show the partial cross-sectional front elevation views of the apparatus for measuring specific gravity during use.
Figure 6B:
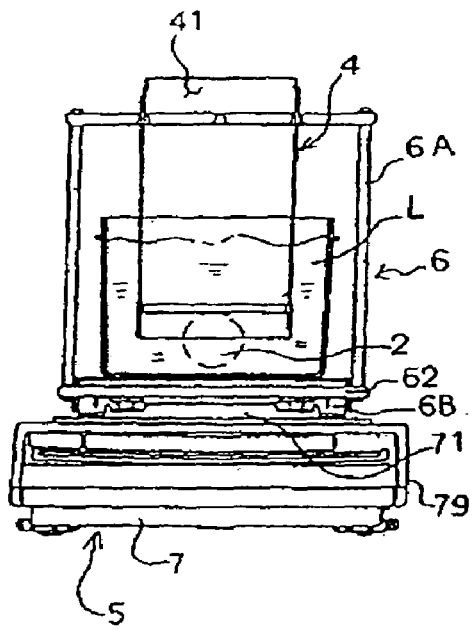

FIGS. 6A and 6B show partially cross-sectional front elevation views of the specific gravity measuring apparatus 5, wherein the specimen mounting unit 6 and the electronic weighing scale 7 are incorporated and the solid specimen 2 is held in position. FIG. 6A shows a condition of mounting a solid specimen 2 wherein the specific gravity of which is larger than that of the reference liquid L. FIG. 6B shows another condition of mounting a solid specimen 2 where the specific gravity of which is smaller than that of the reference liquid L. In these conditions, the lower frame 62 is placed on the weighing pan 71 of the electronic weighing scale 7, and the liquid bath mounting platform 6B is placed on a frame base 79 of the electronic weighing scale 7.

Figure 7:
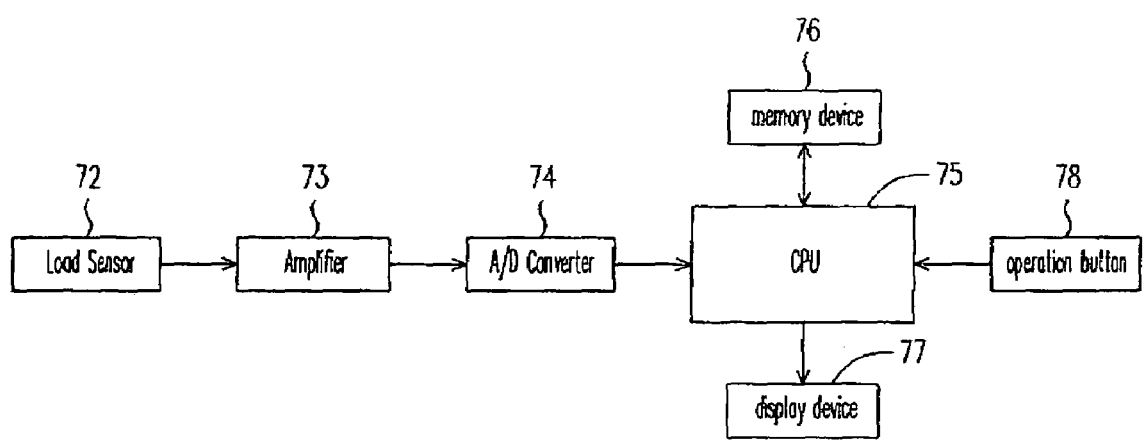
FIG. 7 shows a block diagram of an electronic weighing scale associated with an example of the present invention.
Figure 8:
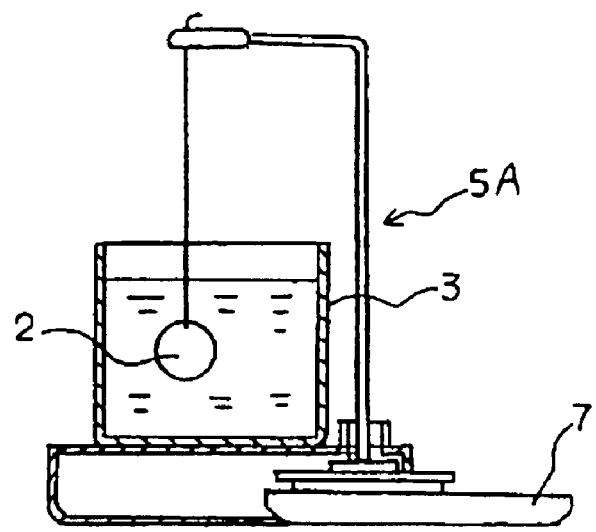
FIG. 8 is a partial cross-sectional front elevation view showing a configuration of a conventional apparatus for measuring specific gravity.
Figure 9:
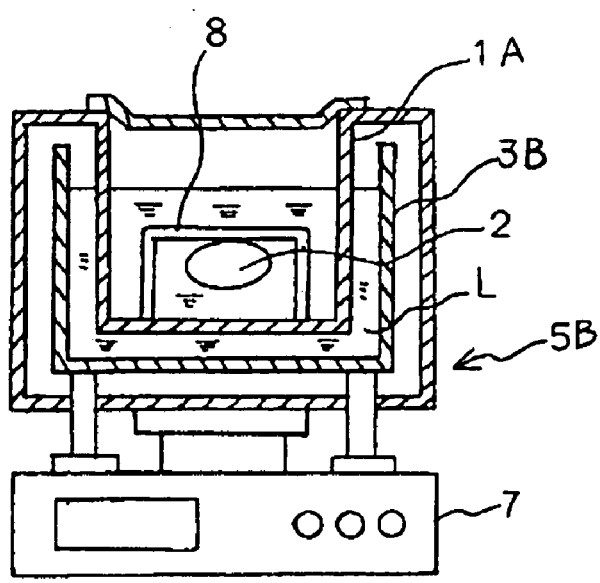
FIG. 9 is a partial cross-sectional front elevation view showing a configuration of another conventional apparatus for measuring specific gravity.

FIG. 7 shows a block diagram of the electronic weighing scale 7. The electronic weighing scale 7 uses a load sensor 72 to convert a weight load applied to the weighing pan 71 into electrical signals. After the electrical signals are amplified by an amplifier 73, the amplified electrical signals are converted into digital signals by an A/D converter 74. The digital signals are input into a CPU 75 constituting a microcomputer, and are subjected to calculations according to the aforementioned Equations (4) and (5) stored in a memory device 76. Data of specific gravity values calculated are displayed on a display device 77. The electronic weighing scale 7 is also equipped with operation buttons 78 providing instructions for differentiating the weights measured by the weighing pan 71 as well as for the start of the calculation process.

A method of measuring the specific gravity of the solid specimen 2 by means of the specific gravity measuring apparatus 5 is described hereinafter with reference to FIGS. 6A, 6B and 7. First, the weight (W0) of the underwater weighing container unit 4 itself, i.e., the underwater weighing container unit 4 together with the frame 6A are measured, and the operation buttons 78 is pressed to store the data of W0 in the memory device 76. Then, the weight (W1) of the aerial weighing container 41 holding the solid specimen 2 is measured, and the corresponding data is stored in the same manner. If the specific gravity of the solid specimen 2 is larger than that of the reference liquid L, the solid specimen 2 is placed at the position as shown in FIG. 6A to measure the weight W2, and the relevant data is recorded in the same manner. The operation buttons 78 is pressed to allow the CPU 75 to start calculating the stored data based on the aforementioned Equation (4), and then the specific gravity of the solid specimen 2 are calculated and displayed.

If the specific gravity of the solid specimen 2 is smaller than that of the reference liquid L, the solid specimen 2 is inserted in the position set forth in FIG. 6B for measuring the weight W3. Subsequently, the operation buttons 78 is pressed to allows the CPU 75 to start calculating these stored data based on the aforementioned Equation (5), and then the specific gravity of the solid specimen 2 are calculated and displayed.

As described heretofore, and as shown by the underwater weighing container 1 in FIGS. 2A and 2B and the underwater weighing container unit 4 in FIG. 4, the present invention is characterized in that a single and compact structure capable of weighing the solid specimen 2 immersed in the reference liquid L because the structure comprises the bottom plate 12 movable upwardly and downwardly in a given range within the tubular body 11. Based on this configuration, the solid specimen 2 that will sink in the reference liquid L can be placed on the upper surface of the bottom plate 12 in the reference liquid L. While the solid specimen 2 that will float in the reference liquid L can be inserted underneath the bottom plate 12. In this way, the weight of the solid specimen 2 can be measured in the reference liquid L. While several examples of the present invention are disclosed herein, the conceivable configurations according to the present invention are not limited to these embodiments. For example, the tubular body 11 can be provided with a guide that will help to prevent the bottom plate 12 from tilting during moving the bottom plate 12 upward or downward. By increasing the number of coupling rods 42, it is possible to hang and hold the tubular body 11 more securely.

While the present invention has been described with a preferred embodiment, this description is not intended to limit our invention. Various modifications of the embodiment will be apparent to those skilled in the art. It is therefore contemplated that the appended claims will cover any such modifications or embodiments as fall within the true scope of the invention.

What is claimed is:

1. A method for measuring specific gravity using an underwater weighing container the underwater weighing container comprising a body having a side wall defining a hollow space, an upper open end, and a bottom open and; and a bottom plate placed in the body which is movable both upwardly and downwardly along an axial direction of the body in a given range between the upper open end and the bottom open end for holding a solid specimen, wherein the underwater weighing container receives a weight or a buoyant force of the solid specimen immersed in a reference liquid, the method comprising:

weighing the solid specimen in air;
   weighing the underwater weight container without the solid specimen while the underwater weight container is immersed in a reference liquid; and
   weighing the underwater weight container and the solid specimen while the underweight container with the solid specimen is immersed in the reference liquid, wherein
   the solid specimen is placed on an upper surface of the bottom plate so that the weight of the solid specimen is applied to the bottom plate if a specific gravity of the solid specimen is greater than that of the reference liquid, or
   the solid specimen is inserted underneath the bottom plate so that the buoyant force from the solid specimen is applied to the bottom plate if the specific gravity of the solid specimen is smaller than that of the reference liquid.

2. A method for measuring specific gravity using a specific gravity measuring apparatus, the specific gravity measuring apparatus comprising an underwater weighing container having a body with a side wall defining a hollow space, the body having an upper open end and a bottom open end, a bottom plate being placed in the body which is movable both upwardly and downwardly along an axial direction of the body in a given range between the upper open end and the bottom open end for holding a solid specimen, the underwater weighing container receiving a weight or a buoyant force of the solid specimen immersed in a reference liquid, the method comprising:

weighing the solid specimen in air;
   weighing the underwater weight container without the solid specimen while the underwater weight container is immersed in a reference liquid; and
   weighing the underwater weight container and the solid specimen while the underwater weight container with the solid specimen is immersed in the reference liquid, wherein
   the solid specimen is placed on an upper surface of the bottom plate so that the weight of the solid specimen is applied to the bottom plate if a specific gravity of the solid specimen is greater than that of the reference liquid, or
   the solid specimen is inserted underneath the bottom plate so that the buoyant force from the solid specimen is applied to the bottom plate if the specific gravity of the solid specimen is smaller than that of the reference liquid.

3. An underwater weighing container unit, comprising:

an underwater weighing container having a body with a side wall defining a hollow space, the body having an upper open end and a bottom open end, a bottom plate placed in the body which is movable both upwardly and downwardly along an axial direction of the body in a given range between the upper open end and the bottom open end for holding a solid specimen inside, the underwater weighing container receiving a weight or a buoyant force of a solid specimen immersed in a reference liquid;
   an aerial weighing container to receive the weight of a solid specimen in air;
   a frame supporting the underwater weighing container; and
   a weight measuring unit.

4. A method for measuring specific gravity using the underwater weighing container according to claim 3 comprising:

weighing the solid specimen on the underwater weight container in air by placing the solid specimen in the aerial weighing container;
   weighing the underwater weight container without the solid specimen while the underwater weight container is immersed in the reference water; and
   weighing the underwater weight container and the solid specimen while the underwater weight container with the solid specimen is immersed in the reference liquid, wherein
   the solid specimen is placed on an upper surface of the bottom plate so that the weight of the solid specimen is applied to the bottom plate if a specific gravity of the solid specimen is greater than that of the reference liquid, or
   the solid specimen is inserted underneath the bottom plate so that the buoyant force from the solid specimen is applied to the bottom plate if the specific gravity of the solid specimen is smaller than that of the reference liquid.

5. An underwater weighing container comprising:
a body having a side wall defining a hollow space, an upper open end, and a bottom open end;
a bottom plate placed in the body which is movable both upwardly and downwardly along an axial direction of the body in a given range between the upper open end and the bottom open end for holding a solid specimen, wherein the underwater weighing container receives a weight or a buoyant force of the solid specimen immersed in a reference liquid;
an aerial weighing container to receive the weight of the solid specimen in air;
a frame supporting the underwater weighing container; and
a weight measuring unit.

6. A method for measuring specific gravity using the underwater weighing container according to claim 5 comprising:
weighing the solid specimen on the underwater weight container in air by placing the solid specimen in the aerial weight container;
weighing the underwater weight container without the solid specimen while the underwater weight container is immersed in the reference water; and
weighing the underwater weight container and the solid specimen while the underwater weight container with the solid specimen is immersed in the reference water, wherein
the solid specimen is placed on an upper surface of the bottom plate so that the weight of the solid specimen is applied to the bottom plate if a specific gravity of the solid specimen is greater than that of the reference liquid, or
the solid specimen is inserted underneath the bottom plate so that the buoyant force from the solid specimen is applied to the bottom plate if the specific gravity of the solid specimen is smaller than that of the reference liquid.

7. The underwater weighing container according to claim 5, further comprising a rim provided at the bottom end of the body for engaging with the bottom plate.

8. The underwater weighing container according to claim 5, further comprising a stopper provided on the side wall inside the hollow space of the body for engaging with the bottom plate.

9. The underwater weighing container according to claim 5, wherein the bottom plate has a mesh or porous structure.

* * * * *